United States Patent [19]

Kubota

[11] Patent Number: 5,422,107
[45] Date of Patent: Jun. 6, 1995

[54] TRICHODERMA HARZIANUM SK-55 FUNGUS, FUNGICIDE CONTAINING IT, AND METHOD OF MANUFACTURE OF THE SAME AND ITS USE

[75] Inventor: Terumasa Kubota, Kawachinagano, Japan

[73] Assignee: Hokkaido Green Kosan, Incorporated, Hokkaido, Japan

[21] Appl. No.: 172,273

[22] Filed: Dec. 23, 1993

[30] Foreign Application Priority Data

Dec. 25, 1992 [JP] Japan .................................. 4-359484

[51] Int. Cl.$^6$ ......................... A01N 63/00; A01N 1/00; A61K 37/00; C12N 1/14
[52] U.S. Cl. .................................. 424/93.5; 435/254.1; 435/945; 47/58
[58] Field of Search .................. 424/93 Q, 93 R, 93.1, 424/93.5; 435/254, 254.1, 945; 47/57.6, 58, DIG. 9, DIG. 10, DIG. 11

[56] References Cited

U.S. PATENT DOCUMENTS 4,713,342 12/1987 Chet et al. ........................ 435/254

*Primary Examiner*—David T. Fox
*Assistant Examiner*—Erich E. Veitenheimer
*Attorney, Agent, or Firm*—Wenderoth, Lind & Ponack

[57] ABSTRACT

The fungus *Trichoderma harzianum* SK-55 provides broad antagonistic interaction against plant pathogenic diseases, and may be used to control fungal diseases in plants. A fungicidal composition contains *Trichoderma harzianum* SK-55 isolated from the soil. A method of manufacturing a fungicidal composition comprises introducing a large quantity of *Trichoderma harzianum* SK-55 into a culture medium, incubating it on the culture medium at a specific temperature range and at a specific humidity for a specific period of time, drying it at a specific low temperature range, and, if necessary, milling it into specific grain sizes. The fungicidal composition containing the incubated fungus may be distributed at the rate of 0.5 g to 5 g/m$^2$.

7 Claims, No Drawings

TRICHODERMA HARZIANUM SK-55 FUNGUS, FUNGICIDE CONTAINING IT, AND METHOD OF MANUFACTURE OF THE SAME AND ITS USE

BACKGROUND OF THE INVENTION

1. Field of the Invention

The present invention relates to *Trichoderma harzianum* SK-55 fungus (which is deposited under No. 13327 and International deposit No. Ferm. BP 4346, at a patent microorganism depository, the National Institute of Bioscience and Human-Technology (NIBH), Japan) that provides a wide range of antagonism against fungal diseases in plants, whereby those plant diseases caused by fungi can be controlled. The present invention also provides a method of manufacturing fungicide that contains the *Trichoderma harzianum* SK-55 fungus, and the use of the same.

2. Description of the Prior Art

In the prior art, agricultural chemicals that contain chemical compounds synthesized chemically are generally used to control plant diseases caused by soil-borne pathogenic fungi. For those years, the demands for protecting the natural environment and conserving the natural resources are important, and it is more interesting to provide a biological fungicide that is not harmful to humans, animals or plants.

In this respect, fungi of the Tricoderma species are of particular interest because of their effective and useful control of the dense growth of fungi that is promoted by the lysis, biotrophic myco-parasite and competition of the fungi.

For example, it is recognized that the fungi of the Tricoderma species may provide the fungicide effect if their conidia or chlamydospores or the antagonistic microorganism in their extractions are utilized (Japan unexamined patent publication No. 1-102010).

It is also reported that an aqueous Tricoderma sp. -35/84 spore suspension can advantageously be used for controlling the Pythium fungi in particular (Japan unexamined patent publication No. 2-245178). Furthermore, it is reported that the *Tricoderma harzianum* T315 fungus has resistance to chemical fungicides, and may provide higher fungicidal control against more kinds of fungi when it is combined with any other chemical fungicides (European patient specification No. 0133 878 B1).

Those kinds of fungi which have been reported as providing the antifungal activity as mentioned above are disadvantageous because they are not economical for practical use, have limited capability of controlling the plant diseases caused by fungi, and may cause environmental pollution or harm to humans, animals, plants, etc.

It is known that 80% of the plant diseases are caused by the soil-borne pathogetic fungi. It might therefore be possible to control such fungal diseases by preventing the growth of the pathogenic fungi more effectively, but there are many cases where in this way, the symptoms of the diseases caused by those kinds of pathogenic fungi which are usually identified as the sources of the diseases cannot appear even if a host is inoculated with those pathogenic fungi. This is principally because the appearance of the disease symptom is associated with the interaction of the particular fungi (which applies particularly to lawns). For practical purposes, the antifungal control may be achieved by using any suitable chemicals that provide a broad range of antifungal action.

The above observation applies similarly to biological control which has similar problems and cannot be utilized for practical purposes. Those problems lie in the selection of any strains that provide the broad antagonistic interaction, the high settlement of such strains in the soil and plant root, and the growth of mycelia which cannot be influentially controlled by any external factors.

SUMMARY OF THE INVENTION

An effort has been attempted to find any strain that provides the broad antagonistic action against the fungal diseases and can settle well in the soil, and strains of *Trichoderma harzianum* SK-55 species have been successfully discovered from the soil in the Tokachi mountains, Hokkaido, Japan. Those strains have been isolated from the soil there.

It is therefore the object of the present invention to provide such strains of *Trichoderma harzianum* SK-55, thereby solving the problems described above in reference to the prior art.

Specifically, the present invention provides a fungicidal composition against plant diseases that comprises *Trichoderma harzianum* SK-55 fungus obtained by isolating it from the soil in the Tokachi mountains, Hokkaido, Japan. The present invention also provides a fungicide against plant diseases that contains a large amount of *Trichoderma harzianum* SK-55 grown on a culture medium.

Furthermore, the present invention provides a method of manufacture of a fungicide against plant diseases, which comprises inoculating a fungus *Trichoderma harzianum* SK-55 in a bran which contains a specific moisture and has previously been sterilized, incubating said fungus *Trichoderma harzianum* SK-55 carried on said sterilized bran at a specific temperature range and at a specific humidity range for a specific number of hours, followed by drying it at low temperature, and, if necessary, pulverizing it into specific grain sizes. In one preferred embodiment, fungus Trichoderma harzianum SK-55 may be incubated at 20° C. to 30° C. and at relative humidity above 90%, for seven (7)to ten (10) days, and may be dried at 30° C. to 40° C.

The present invention provides possible uses of a fungicide against the plant diseases obtained by incubating fungus *Trichoderma harzianum* SK-55 according to the method of the present invention, wherein the fungicide may be distributed againt particular plants at the rate of 0.5 g to 5 g/m$^2$. In one specific example of use, 0.5 g to 5 g of fungicide containing fungus *Trichoderma harzianum* SK-55 thus incubated is diluted with an additive, and 500 g to 1,000 g (1 kg) of dilution is obtained. The resultant dilution may be distributed againt particular plants at the rate of 500 g to 1 kg/m$^2$. In another possible use, 0.5 g to 5 g of fungicide containing fungus *Trichoderma harzianum* SK-55 cultured as above may be diluted with water to obtain 1 l to 5 l of dilution, and the resultant dilution may be distributed against particular plants at the rate of 1 l to 5 l/m$^2$.

The strains of *Trichoderma harzianum* SK-55 provided by the present invention have been deposited under No. 13327 and International deposit No. Ferm. BP 4346, patent microorganism depository, the National Institute of Bioscience and Human-Technology (NIBH) (formerly Fermentation Research Institute), Japan.

As one of the features of the present invention, the strains of *Trichoderma harzianum* SK-55, which for example are incubated in a suitable culture medium such as a potato dextrose agar, produce a strong coumarin-like flavor component, or look like a dark green color as compared with other conventional strains of Trichoderma species. *Trichoderma harzianum* SK-55 according to the present invention should be considered as marking an epochmaking milestone, as it is actually recognized that it may provide antibiosis, may be capable of being a biotrophic myco-parasite to plant fungus, may be capable of competition, and may produce enzyme.

*Tricoderma harzianum* SK-55 according to the present invention has been determined qualitatively, as follows:

Qualitative determination method: as a preliminary step, each of the soil-borne pathogetic fungi of interesst as well as *Trichoderma harzianum* SK-55 is incubated in a suitable culture medium such as a potato dextrose agar on a petri dish, at a suitable temperature and for a suitable period of time depending upon each kind of fungi.

After each pathogenic fungus has been incubated on a flat plane, it is stamped out by a 12 mm-diameter borer and is then placed in the center of 90 mm-diameter petri dish containing culture medium. *Trichoderma harzianum* SK-55 which has thus been incubated is stamped out by a 7 mm-diameter borer and then placed on each stamped-out fungus on its petri dish. Then, they are incubated on the petri dish in order to examine their antagonistic interaction.

Typical samples of the fungi that are capable of being subcultured are taken and sorted according to each subdivision in each fungus division, and they are examined visually to see how the antagonistic interaction takes place. The results are shown in Tables 1 and 2 hereinafter.

In the second column "Growth Inhibition" of the Tables 1 and 2, +++ shows fungal growth inhibition that takes effect immediately, ++ shows the fungal growth inhibition that takes effect 10 days after the appropriate fungus is incubated, and + shows that fungi lysis takes place within 20 days and then the fungal growth inhibition takes effect.

It may be appreciated from the results in the tables that *Trichoderma harzianum* SK-55 according to the present invention can provide fungal growth inhibition against any of the pathogenic fungi listed in the tables, although the growth inhibition may take effect later (not later than 20 days) for some pathogenic fungi.

As a general tendency, the fungal growth inhibition will not take immediate effect for some fungi that have a higher rate of growth, but will eventually take effect as the fungi lysis takes place later.

In one embodiment of the present invention, the method of manufacturing a fungicide that contains the fungus *Trichoderma harzianum* SK-55 according to the present invention is described. The fungicide obtained according to the method is easily stored and transported.

A bran is provided, to which an equal amount of water is added. Then, the bran containing the water is sterilized at 120° C., and is cooled to the room temperature. Then, a fungus to be seeded is inoculated into the bran. The resulting bran is placed on a tray such that it is flat to the thickness of less than 5 cm, and is incubated at 25° C. and at the relative humidity above 90% for seven (7) days.

At the end of incubation process, the bran is exposed to the dry air that has been dehumidified, and is dried under 40° C. until it contains less than 8% of moisture.

After the bran has been dried, it is pulverized into 80 mesh pass grain size. It is found that the fungus can be stored in its pulverized form for one year without diminishing. An aqueous suspension is obtained, and is sprayed into the soil. It is also found that it provides good results.

The powdery fungicide, obtained in the above procedure, usually contains $1 \times 10^9$ to $1 \times 10^{10}$ conidia per one gram of the fungicide.

In one preferred example of use, the powdery fungicide obtained according to the present invention may be used for the specific purpose of controlling the fungal diseases in plants. The steps of using it are described below.

An experiment was conducted on using the powdery fungicide for protecting plants against fungi in the soil or for recovering the plants from the diseases caused by the fungi, and the results show that 0.5 g to 1.0 g/m$^2$ of powdery fungicide may be used for protecting plants against fungi, and 1.0 g to 5 g/m$^2$ may be used for recovering the plants from the diseases. Practically, when a smaller quantity of powdery fungicide is used, it cannot be distributed uniformly. Therefore, the plants cannot be recovered uniformly. This problem may be solved by diluting a small quantity of fungicide with water, soil, and/or any organic additive.

When soil or additive is used as a diluent, 0.5 g to 5 g of powdery fungicide may be diluted at the rate of 500 g to 1 kg/m$^2$ of the diluent, and the resulting dilution may be distributed. When any solid substance is used as a diluent, it is better that the resulting dilution is first distributed, and then water is distributed. This helps the fungicide settle well in the soil.

When water is used as a diluent, 0.5 g to 5 g of powdery fungicide may be diluted at the rate of 1 l to 5 l/m$^2$ of water, and may be distributed in the aqueous suspension. When the soil has a good drainage condition, the powdery fungicide may be diluted at the higher rate, and then the fungicide can settle better and more uniformly.

The following describes the case in which the fungicide of the invention is used on golf greens.

Before using the fungicide, the bent grass greens on the golf course were found to suffer from the fungal disease caused by *Rhizoctonia solani*. Brown patches occurred on the greens. The powdery fungicide was diluted at the rate of 3 g to 2 l/m$^2$ of water, and the resulting dilution was distributed. In two days, the disease symptom disappeared, and in twelve days, the greens were recovered from the disease, regaining the original normal condition.

The amount of the fungicide that remained in the soil since it was distributed was great for the first ten days, but decreased over time until finally it was negligible after 60 days.

The fungicide was used at the soil temperature of 15° C. to 25° C. in the before described preferred example of use. When it is used below 15° C., it will remain static, and is expected to survive longer.

In the before described preferred example of use, the mixing ratio between the powdery fungicide and the diluent and the distributing ratio onto the soil have been determined from the viewpoint of the cost efficiency for practical use. Even if these ratios are beyond the before described respective limits, the efficiency remains as it is.

It is clear from the above result that the microorganisms in the soil can have a constant phase for an extended period of time, and can remain as they are.

It should be noted that the powdery fungicide contains no other component than the bran and fugicidal components. Thus, it does no harm to humans, animals, fishes, and so on, and can effectively control the fungal diseases in plants. It can be used as the ideal fungicide.

The fungicide that contains *Trichoderma harzianum* SK-55 strain according to the present invention provides a combination of actions that include the ability to release antibiotics, the ability of being parasite to any pathogenic fungi, the ability of being biotrophic mycoparasite, the capability of competition, the generation of enzyme, and so on, and may be effective for all kinds of fungi that may affect lawns and other plants and may be useful in controlling those fungi.

When the fungicide according to the present invention is actually used for a particular plant, the minimum quantity may provide the maximum effect. It persists for a certain period of time, after which it will disappear (does not remain) by itself over time.

According to the method of the invention, the fungicides can be provided on a mass production basis, and can be handled and used easily. For example, when the fungicide is used on golf greens, it may be contained in a spray of water. So, there is no extra labor of distributing the fungicide alone.

DESCRIPTION OF PREFERRED EMBODIMENTS

The present invention is described in further detail with reference to particular preferred embodiments thereof.

Embodiment 1

10 kg of bran, 10 l of water and 50 ml of concentrated hydrochloric acid (36%) are provided and mixed together. The resultant mixture is then sterilized at 120° C. for 30 minutes in a trommel-type sterilizer vessel.

In the meantime, the fungus *Trichoderma harzianum* SK-55 has previously been incubated in a liquid medium which is shaken, and a *Trichoderma harzianum* SK-55 fungus to be seeded has been obtained. Then, 100 ml of this fungus is added to the above sterilized bran and inoculated therein.

The resulting bran is placed onto each of 20 aluminum-made incubating trays (450 mm × 700 mm × 80 mm each) where it is incubated for 7 days under the ambient condition at 25°±1° C. and at the relative humidity of 90%.

To promote the generation of conidia, the bran on each tray is stirred one time for each of the fifth and subsequent days after the incubation began.

At the end of the incubation process, the bran is exposed to dry air at 35° C. and is dried for about twelve hours until it contains less than 4% of moisture. The resultant dried bran weighs 7.3 kg. It is then pulverized by an impact milling machine into 80 mesh pass grain sizes which may be used as a powdery fungicide that controls fungal diseases in plants. The fungicide contains $8 \times 10^9$ conidia per one gram.

Embodiment 2

An aqueous suspension that contains 5 g of *Trichoderma harzianum* SK-55 strain in its powdery form and 1 l of water is obtained, and is distributed, at the rate of 1 m², onto the part of the particular plant affected by a particular fungus. As a preventive measure, an aqueous suspension containing 0.5 g of *Trichoderma harzianum* SK-55 fungus and 1 l of water may be distributed on plants. This may protect those plants against fungi in the soil as well as remove any plant diseases caused by the fungi.

Embodiment 3

A fungicide composition contains 5 g of *Trichoderma harzianum* SK-55 strain in its powdery form, which is the same as that in the previous embodiment 1, and its carrier such as 500 g of peat moss or matured compost. When this fungicide is used as a remedy, it may be distributed to the root of a plant affected by the fungal disease, at the rate of 1 m².

When it is used as a preventive measure, the composition of 1 g of *Trichoderma harzianum* SK-55 fungus and its carrier may be distributed at the rate of 1 m².

As the preventive measure or for better germination, the composition may contain 100 g of lawn seeds and 50 g of *Trichoderma harzianum* SK-55 fungus mixed together, and may be inoculated in the soil.

Although the present invention has been described with reference to the particular preferred embodiments thereof, it should be understood that various changes and modifications may be made without departing from the spirit and scope of the invention as defined in the appended claims.

TABLE 1

| Growth Inhibition for each Subdivision of Fungus | | |
|---|---|---|
| Name of Fungus | | Growth Inhibition |
| MASTIGDMYCOTINA | | |
| *Pythium aphanidermatum* | | + + |
| *Phytophthora infestans* | MAFF02-35883 | + + + |
| *Aphanomyces cochlioides* | MAFF03-05845 | + + + |
| ZYGOMYCOTINA | | |
| *Rhizopus javanicus* | MAFF03-05207 | + |
| *Mucor inaequisporus* | IF08635 | + + |
| ASCOMYCOTINA | | |
| *Neurospora crassa* | IF032307 | + |
| *Nectria multiloculata* | IF031040 | + + + |
| *Glomerella fructigena* | IF05951 | + + + |
| *Cochliobolus cynodontis* | MAFF03-05369 | + + + |
| *Micronectriella nivalis* | | + + + |
| *Sclerotinia borealis* | | + + + |

+ + +: fungal growth inhibition takes effect immediately.
+ +: fungal growth inhibition takes effect 10 days after incubation.
+: fungal lysis takes place within 20 days followed by fungal growth inhibition (also apply to Table 2).

TABLE 2

| Growth Inhibition for each Subdivision of Fungus | | |
|---|---|---|
| Name of Fungus | | Growth Inhibition |
| BASIDIOMYCOTINA | | |
| *Typhula ishikariensis* | | + + + |
| *Typhula incarnata* | | + + + |
| DEUTEROMYCOTINA | | |
| *Rhizoctonia solani* | | + + + |
| *Verticillium dahliae* | MAFF01-03001 | + + + |
| *Alternaria brassicae* | MAFF07-12096 | + + + |
| *Curvularia geniculata* | MAFF03-05365 | + + + |
| *Helminthosporium dactylidis* | MAFF05-10940 | + + + |
| *Phoma destructiva* | MAFF03-05182 | + |
| *Botrytis cinerea* | MAFF03-05539 | + + + |
| *Fusarium oxysporum* | | + |
| *Gloeosporium musarum* | MAFF03-05595 | + + + |

I claim:

1. A fungicidal composition containing *Trichoderma harzianum* SK-55 fungus isolated from soil.

2. A fungicidal composition containing $1 \times 10^9$ to $1 \times 10^{10}$ conidia, per one gram of the composition, of *Trichoderma harzianum* SK-55 fungus grown on a culture medium.

3. A method of manufacturing a fungicidal composition, comprising:

introducing *Trichoderma harzianum* SK-55 fungus into a sterilized bran containing moisture;

incubating said fungus carried on said sterilized bran at a temperature ranging between 20° C. and 30° C. and at a relative humidity above 90% for a period of time ranging between seven days and 10 days; and drying said incubated fungus at a temperature ranging between 30° C. and 40° C.

4. A method of manufacturing a fungicidal composition, comprising:

introducing *Trichoderma harzianum* SK-55 fungus into a sterilized bran containing moisture;

incubating said fungus carried on said sterilized bran at a temperature ranging between 20° C. and 30° C. and at a relative humidity above 90% for a period of time ranging between seven days and 10 days;

drying said incubated fungus at a temperature ranging between 30° C. and 40° C.; and pulverizing said dried fungus into 80 mesh pass grain size.

5. A method of protecting plants against fungus, which comprises applying to the plants a fungicidal amount of a fungicidal composition containing incubated *Trichoderma harzianum* SK-55 fungus, wherein said fungicidal composition is applied at a rate of 0.5 g to 5 g/m².

6. A method of protecting plants against fungus, which comprises applying to the plants a fungicidal amount of a fungicidal composition containing incubated *Trichoderma harzianum* SK-55 fungus, wherein each 0.5 g to 5 g of said fungicidal composition is diluted with 500 g to 1 kg of a diluent, and the diluted composition is applied at a rate of 500 g to 1 kg/m².

7. A method of protecting plants against fungus, which comprises applying to the plants a fungicidal amount of a fungicidal composition containing incubated *Trichoderma harzianum* SK-55 fungus, wherein each 0.5 g to 5 g of said fungicidal composition is diluted with 1 l to 5 l of water, and the diluted composition is applied at a rate of 1 l to 5 l/m².

* * * * *